United States Patent [19]

Ross et al.

[11] 4,157,278

[45] Jun. 5, 1979

[54] IMMUNOSTIMULATORY AGENTS

[75] Inventors: Gordon W. Ross, Ruislip; Monica J. Gardner nee Marshall, North Harrow; Walter Wolff, London, all of England

[73] Assignee: Glaxo Laboratories Limited, Greenford, England

[21] Appl. No.: 888,782

[22] Filed: Mar. 21, 1978

[30] Foreign Application Priority Data

Mar. 22, 1977 [GB] United Kingdom ............... 12090/77

[51] Int. Cl.$^2$ .......................... C12B 1/00; C12B 1/00; A61K 37/00

[52] U.S. Cl. ......................................... 195/4; 195/2; 195/29; 424/177

[58] Field of Search .................. 424/177; 195/2, 4, 29

[56] References Cited

U.S. PATENT DOCUMENTS

| | | | |
|---|---|---|---|
| 3,616,243 | 10/1971 | Kawaji | 195/29 |
| 3,716,452 | 2/1973 | Kitomura et al. | 195/2 |
| 3,855,197 | 12/1974 | Hirsch et al. | 195/29 |
| 3,868,303 | 2/1975 | Tsumura et al. | 195/29 |
| 3,876,779 | 4/1975 | Adam et al. | 195/2 |
| 3,917,510 | 11/1975 | Kitomura et al. | 195/2 |
| 3,976,544 | 8/1976 | Adam et al. | 195/4 |
| 4,013,788 | 3/1977 | Jolles et al. | 424/177 |
| 4,032,663 | 6/1977 | Kobayashi | 195/2 |
| 4,036,953 | 7/1977 | Adam et al. | 195/4 |

FOREIGN PATENT DOCUMENTS

| | | | |
|---|---|---|---|
| 1046770 | 5/1963 | United Kingdom | 195/2 |
| 1426042 | 2/1973 | United Kingdom | 195/2 |

OTHER PUBLICATIONS

S. Kotani et al., Biken Journal, vol. 18, 105-111 (1975).
F. Audibert et al., Cellular Immunology 21, 243-249 (1976).
A. Adam et al., Biochem and Biophys, Res. Commun. 72, 1976, 339-346.
D. Perlman, Chem. Abst. vol. 84, 1976.
Kotani et al., Biken Journal, vol. 18, 77-92, 1975.

*Primary Examiner*—Delbert R. Phillips
*Attorney, Agent, or Firm*—Bacon & Thomas

[57] ABSTRACT

This invention relates to a process for the production of water-soluble fractions from *Streptomyces griseus* mycelium and containing peptidoglycan material having immunostimulatory properties and to formulations containing such fractions. Several examples of the process are given.

25 Claims, No Drawings

IMMUNOSTIMULATORY AGENTS

This invention relates to a process for the production of water-soluble fractions containing peptidoglycan material having immunostimulatory properties and to formulations containing such fractions.

In recent years many preparations from micro-organisms have been suggested as immunostimulatory agents in order, for example, to increase host resistance to infections caused by viruses or micro-organisms. In particular whole mycobacterial cells have been used for many years for their adjuvant effect in enhancing the production of antibodies to a selected antigen and it is well known that mycobacterial cell walls and wax fractions from such cell walls exhibit adjuvant activity.

The use, however, of repeated doses of whole mycobacterial cells in human patients can give rise to undesirable side effects such as pyrexia and malaise, increased sensitivity to, for example, tuberculin or endotoxin, hypertrophy of the lymphoid organs or formation of local granulomata and this has resulted in much recent effort being concentrated on the isolation and identification of active fractions from mycobacteria and other micro-organisms which lack significant toxic activity. It is generally preferred that such immunostimulatory fractions be water-soluble as this is likely to diminish local reactions and also makes purification of the fractions easier to achieve. A large number of fractions have been isolated from mycobacteria and are reported as having immunostimulatory activity without significant toxic properties. Some other micro-organisms have also been investigated.

A disadvantage of the use of mycobacteria is that mycobacterial cultures are relatively slow-growing and it is difficult to produce the large yields of cells required for commercial production. Furthermore the actual yield of immunostimulatory material from each cell is low and large amounts of cell material are required for isolation of the required component of the cell wall.

We have examined a number of micro-organisms for immunostimulatory fractions that might meet the requirements outlined above and have found that water-soluble fractions having immunostimulatory activity may be extracted from *Streptomyces griseus* mycelium in surprisingly high yield. These fractions are effective in stimulating both humoral and cell mediated immunity and have shown no signs of undesirable toxic effects.

It has been proposed to isolate from the protoplasmic material of the mycelium of Streptomyces species certain oligonucleotides which are said to have therapeutic activity. We prefer to remove nucleic acid material from our immunostimulatory fractions since nucleic acid materials can have inherent toxicity.

According to one feature of the present invention there is provided a process for the production of a water-soluble fraction containing peptidoglycan material having immunostimulatory activity wherein the mycelium of a strain of *Streptomyces griseus* is treated to solubilise bound peptidoglycan components of the cell walls thereof to yield a fraction containing the desired immunostimulatory activity, said process including the step of separating nucleic acid material from said peptidoglycan fraction.

The term "water-soluble fraction" as used herein is defined as being a fraction which does not sediment from an aqueous medium when centrifuged at 23,000 g for 1 hour.

The definition of the species *Streptomyces griseus* used herein is that given in Bergey's Manual of Determinative Bacteriology, 8th Edition (1974), pages 795 and 799.

In general, the production of the desired immunostimulatory fraction will include some or all of the following steps:
(1) Rupture of mycelial cells
(2) Separation of ruptured cell-walls from mycelial protoplasm
(3) Delipidation of cell-walls
(4) Solubilisation of peptidoglycans in cell-walls
(5) Removal of nucleic acid materials
(6) Removal of unwanted protein and carbohydrate materials.

While it is preferred to rupture the mycelial cells and wash the protoplasm from the insoluble cell-wall material as the initial step prior to solubilisation of peptidoglycans, it is possible to apply the solubilisation treatment directly to the whole cells, which may have previously been delipidated, to yield an aqueous mixture in which water-soluble peptidoglycans are mixed with cell contents and require separation by fractionation techniques designed to remove proteins, nucleic acids etc. The essential step of removal of nucleic acid material is most simply effected by rupturing the cells and washing the cell-walls prior to solubilisation so as to remove all cell-contents including most of the nucleic acid material; further nucleic acid material may be separated from peptidoglycans before or after solubilisation. Similarly, the greater part of the protein and carbohydrate content of the cells is most simply removed by washing the cell-walls prior to peptidoglycan solubilisation but protein and carbohydrate may also be removed in separate steps before or after peptidoglycan solubilisation. Delipidation is preferably effected prior to peptidoglycan solubilisation, most preferably after cell rupture, but may be applied at a later stage.

In general it is preferred to effect the solubilisation of peptidoglycans after the cells have been ruptured and the above purification steps have been applied to the cell-wall material.

The individual process stages are now described in greater detail.

PEPTIDOGLYCAN SOLUBILISATION

In order to solubilise the bound peptidoglycan components of the mycelial residues, the cell walls or whole cells may be treated with at least one bacteriolytic enzyme that preferably has endoacetylmuramidase activity. The preferred enzyme is egg white lysozyme. Such treatment with egg white lysozyme may be effected at a pH in the range 5 to 8, preferably at pH 6.0 to 6.5, e.g. about 6.2 and at a temperature in the range 15° to 45° C., advantageously an elevated temperature e.g. about 37° C., for a prolonged period, e.g. about 18 hours. Insoluble residues may be removed from the supernatant, e.g. by centrifugation, and are preferably treated with murolytic enzyme for a second time, and the supernatant again separated and combined with the first supernatant.

A bacteriostat is desirably present, for example, toluene.

CELL RUPTURE

Rupture of the cells may be effected, for example, by sonication, by mechanical means e.g. by forcing frozen material through a narrow slit in a Hughes-type extrusion press or grinding in a DYNO-Mill, by freezing and thawing several times or by treatment with an aqueous wetting agent, preferably a long-chain anionic wetting agent e.g. sodium dodecyl sulphate. A preferred method of rupturing the cells is by shaking them with glass beads in buffer, for example, a 0.15 M sodium chloride/0.015 M trisodium citrate buffer at pH 7.

WASHING OF CELL WALLS

After cell rupture, the cell-wall material is advantageously washed exhaustively to remove mycelial protoplasm, e.g. by slurrying in an aqueous medium such as a citrate buffer solution. Where a long-chain anionic wetting agent has been used in cell rupture or in delipidation as mentioned hereinafter, it may be desirable to wash this from the cell-wall material using aqueous urea.

DELIPIDATION

The whole cell or cell wall material is preferably subjected to delipidation prior to solubilisation of peptidoglycans, for example by extraction with hot organic solvents or boiling aqueous detergent. Exhaustive treatment with a succession of organic solvents, e.g. acetone, methanol, ethanol and chloroform, provides an efficient removal of the various lipid components of the cell walls. The use of a boiling aqueous solution of a detergent, preferably a long-chain anionic wetting agent such as, for example, sodium dodecyl sulphate, is particularly effective; this treatment has the added advantage of removing nucleic acid material from the cell wall material. Treatment of mycelial cell wall material, either in the form of whole cells or ruptured cells, with a long-chain anionic wetting agent is thus particularly desirable in the preparation of an intermediate fraction containing the peptidoglycan having immunostimulatory activity and such treatment forms a further feature of the present invention. Alternatively, the solubilised peptidoglycan material can be delipidated by organic solvent extraction procedures.

It will be noted that long-chain anionic wetting agents such as sodium dodecyl sulphate may be used in a single stage to rupture the whole cells, to effect delipidation of the cell wall material and to assist removal of cell contents including nucleic acid material.

REMOVAL OF NUCLEIC ACID MATERIAL

Nucleic acid material may be removed, at least in part, by the washing and delipidating steps referred to above. It is also possible to remove nucleic acid material from the cell wall material by treatment with at least one appropriate enzyme, e.g. a ribonuclease or desoxyribonuclease followed by washing to remove nucleotides so produced. Such enzyme treatment may be applied to the aqueous mixture resulting from peptidoglycan solubilisation, but in this case nucleotides must be removed by fractionation e.g. by molecular sieve techniques such as ultrafiltration or treatment with cross-linked dextrans such as Sephadex, or by ion-exchange chromatography.

Alternatively, the said aqueous mixture may be treated with a selective nucleic acid precipitant.

REMOVAL OF PROTEINS AND CARBOHYDRATES

Removal of unwanted proteins and/or carbohydrates may be effected by treatment with proteolytic and/or glycolytic enzymes. Suitable proteolytic enzymes include, for example, trypsin, chymotrypsin and pronase, the enzymes being used alone or in admixture and if necessary successively. Suitable glycolytic enzymes include, for example $\alpha$-amylase. When the enzymes are applied to cell wall material, the degraded proteins and carbohydrates may be removed by washing. When the enzymes are applied to the solubilised peptidoglycan, fractionation is required as with nucleotide removal.

The aqueous solution containing the active peptidoglycan material may, if desired, be concentrated, optionally treated with an insolubilised proteolytic enzyme such as, for example, trypsin or pepsin, in order to remove any residual murolytic or other enzymes and, as indicated above, small molecules including salts or enzyme degradation products may be removed by molecular fractionation e.g. by molecular sieve techniques such as ultrafiltration or fractionation on cross-linked dextrans or polyamides in neutral or acid aqueous solutions. Freeze-drying of the solution yields a stable flaky powder comprising the active material which is readily soluble in water or buffer solutions.

The mycelium used as starting material may be obtained by culturing *S. griseus* in or on a culture medium therefor and is preferably separated from nutrients before further treatment. *S. griseus* is produced in large quantities from the antibiotics industry, particularly as a by-product of streptomycin manufacture; *S. griseus* is easier to grow on the large scale than, for example, mycobacteria.

Strains of *S. griseus* which may be used include, for example, the streptomycin-producing strains having the following culture collection deposit numbers:

ATCC 15395
ATCC 23345
ATCC 12475
CMI 50967
NCIB 8136
NCIB 8506
NCIB 9001
CBS 16145
CBS 47948
CBS 48148
CBS 90568

All the strains of *S. griseus* that we have tested have, however, yielded a water-soluble fraction containing a peptidoglycan having immunostimulatory activity.

The growth of the *S. griseus* may be carried out according to conventional methods. Thus the nutrient medium used to culture the organism should contain sources of nitrogen and carbon. The nitrogen source may, for example, be a conventional meat or yeast extract, peptone, tryptone or a preparation such as tryptose, casein hydrolysate, meal produced from soya or other vegetable beans, whey powder, distillers' solubles or corn steep liquor. The complex nitrogen source will also be a source of carbon and other useful nutrients. The source of carbon may also, for example, be a carbohydrate source such as glucose, glycerol, starch or any of its breakdown products or other sugars, sugar alcohols, organic acids or paraffins. Sources of sulphur, phosphate, magnesium, calcium, potassium, sodium, iron and trace quantities of other metals and salts may advantageously be present. Depending on the nitrogen and carbon sources present, it may also be beneficial to include salts such as nitrates and sodium or potassium chloride. The optimal pH of the culture medium and the optimal cultivation temperature will depend upon the nature of the organism used. A desirable pH will usually be found in the range pH 4 to 9 and the temperature will generally be in the range 10° to 40° C. Cultivation of the organism will usually be carried out under submerged conditions with stirring or shaking and aeration. Preferred culture conditions include generally temperatures of from 25° to 29° C. and a pH in the range of from 6 to 8, the culture being carried out under aerated submerged conditions for 12 hours to 16 days, preferably 2 to 14 days.

The S. griseus cells may be isolated from the culture medium, for example, by centrifugation and are preferably washed e.g. with distilled water or a dilute sodium chloride solution which may contain citrate buffer to remove contaminating components deriving from the culture supernatant. The cells may then be subjected to further treatment directly or may be stored, for example in frozen form e.g. at −20° C. or in the form of an acetone dried powder.

The water-soluble fractions containing peptidoglycan material obtained by the process of our invention are usable as adjuvants in the immunisation of humans and warm blooded animals against bacterial, parasitic and viral infections such as, e.g., influenza.

Thus another aspect of our invention includes formulations comprising a water-soluble fraction prepared according to the process of our invention in a form suitable for injection e.g. in physiological aqueous solution, as an emulsion or in the form of a liposome. Such formulations may be prepared according to conventional methods. Advantageously the formulations are in the form of dosage units such as ampoules, each unit being adapted to supply a fixed dose of active ingredient. The formulations are intended primarily for administration to humans. Preferred dosage units contain from 0.1 to 2 mg/kg of body weight. Preferably such formulations will be administered to humans by sub-cutaneous injection.

The following non-limiting Examples serve to illustrate the present invention.

EXAMPLE 1

A seed culture of Streptomyces griseus ATCC 15395 was transferred at a 3% level into a culture medium (2 liters) consisting of Oxoid Yeast Extract L21, 6g; Oxoid Peptone L37, 0.6 g; anhydrous potassium dihydrogen phosphate, 1g; magnesium sulphate, $7H_2O$, 0.05 g; glycerol, 20 g; and water, 1 liter; pH adjusted to 7.0. The culture was dispensed in 50 ml amounts into 250 ml conical flasks and grown for 3 days at 28° C. on a 220 rpm shaker.

The cultures were bulked and harvested by centrifugation at 2000 g for 30 min. and the cell pad obtained was washed twice with SSC buffer (0.15M sodium chloride/0.015M trisodium citrate, pH 7) and once with distilled water. Centrifugation at 23,000 g for 1 hour gave a firm pad of wet felt (42 g, dry weight 6.9 g).

A portion of this felt (30.5 g wet weight, 5 g dry weight) was suspended in SSC buffer containing 4% sodium dodecyl sulphate (2.5 liters) and refluxed for one hour. The suspension was subsequently allowed to cool overnight with continuous stirring in a water bath at 25° C. The mycelial residues were harvested by centrifugation at 23,000 g. The mycelial sludge was suspended in SSC buffer (1.2 liters), stirred for 30 minutes at room temperature and then centrifuged at 23,000 g for 1 hour, maintaining the temperature at 25° C. This wash step was repeated twice after which the mycelial residues were suspended in 8M urea (1 liter), stirred overnight, and then given further washes with SSC buffer until the supernatant after centrifugation contained < 5 μg/ml sodium dodecyl sulphate as measured by the method of Hayashi (Anal. Biochem (1975), 67, 503). The mycelial residues were subsequently suspended in 0.02M phosphate buffer pH 7.0 (250 ml) and α-amylase [Sigma, Bacillus subtilis, 50 mg containing 500–1000units/mg] was added thereto together with a few drops of toluene. The resultant mixture was stirred overnight at room temperature, centrifuged at 23,000 g for 1 hour and the pellet obtained was resuspended in SSC buffer (250 ml). The suspension thus obtained was digested at 37° C. with trypsin [Sigma, bovine pancreas, 50 mg containing 10,000–13,000 units/mg] overnight in the presence of a few drops of toluene. The pellet obtained after centrifugation at 23,000 g for 1 hour was washed once in SSC buffer (200 ml) and once in water.

This residue was suspended in 0.05M ammonium acetate pH 6.2 (250 ml), containing egg white lysozyme [Sigma, 25 mg containing 25,000 units/mg] and a few drops of toluene. After overnight incubation at 37° C. with stirring, the insoluble material was removed by centrifugation at 23,000 g for 1 hour and re-extracted with 125 ml of the buffer containing lysozyme. The two lysozyme extracts were combined and desalted by diafiltration on an Amicon 400 ml ultrafiltration apparatus fitted with a UM 05 membrane. By diluting the retentate and reconcentrating twice more, over 97% of low molecular weight solutes were removed. The retained product was freeze-dried to give a solid product (2.1 g, yield 42% of the dry weight of cells).

Analysis of the product indicates that it contains amino acids, principally alanine, glutamic acid, diaminopimelic acid and glycine with some arginine and aspartic acid, the amino sugars glucosamine and muramic acid, and glucose.

The immunostimulatory activity of the product was demonstrated in guinea pigs injected sub-cutaneously with 2×0.25 ml of a water-in-oil emulsion (phosphate buffered saline/Freund's incomplete adjuvant) containing a total of 100 μg of ovalbumin, as antigen, and 100 μg of the product. Increased antibody production and the appearance of cell mediated immunity were readily demonstrated in the presence of this immunostimulatory fraction from S. griseus.

EXAMPLE 2

Washed felt of Streptomyces griseus ATCC 15395 (44 g wet weight, 4 g dry weight), obtained as in Example 1, was suspended in water (200 ml) and acetone (600 ml) was added slowly thereto with vigorous stirring. The resultant mixture was filtered (Whatman No. 54 paper) and the residue was washed with acetone. The acetone-wet felt was packed into a paper thimble and extracted under reflux in a Soxhlet apparatus with each of the following solvents: acetone (16 hrs), ethanol (8 hr), chloroform (16 hrs), chloroform:methanol 87:13 (8 hrs). The extracted felt was subsequently washed once with diethyl ether and finally with acetone. The acetone-moist delipidated felt was suspended in water (800 ml) and the suspension obtained was stirred for ½ hour and then centrifuged at 23,000 g for ½ hour. The residue was washed twice with 0.05 M ammonium acetate, pH 6.2 (800 ml) and then suspended in the same buffer (600 ml) containing egg white lysozyme (Sigma, 60 mg containing 25,000 units/mg) and a few drops of toluene. The resultant mixture was incubated at 37° C. for 18 hours, then centrifuged for 1 hour at 23,000 g. The sediment was redigested with lysozyme as above and recentrifuged. The lysozyme-solubilized extracts were concentrated approx. tenfold by ultrafiltration through a flatbed membrane with a nominal cut-off of 500 M.W. The concentrate thus obtained was diluted with water and reconcentrated to give at least 98% removal of low molecular weight material. The residual retentate was freeze-dried to give a solid product (1.8 g).

Analysis of the product indicated that it contains amino acids, principally alanine, glutamic acid, diaminopimelic acid and glycine with some arginine and aspartic acid, the amino sugars glucosamine and muramic acid and some glucose.

The product was shown to have immunostimulatory activity according to the method described in Example 1.

EXAMPLE 3

*Streptomyces griseus* NCIB 11398 was grown and harvested by the method of Example 1. The yield of washed felt was 46 g wet weight, 9.6 g dry weight.

A portion of this felt (24 g wet weight, 5 g dry weight) was then treated by the method of Example 1 and the retentate after ultrafiltration freeze-dried to give a solid product (0.72 g).

Analysis of the product showed that the principal amino acids were alanine, diaminopimelic acid, glutamic acid and glycine. It also contained glucosamine, muramic acid and glucose.

Increased antibody production and the appearance of cell mediated immunity were readily demonstrated in the presence of the product by the technique described in Example 1.

EXAMPLE 4

*Streptomyces griseus* NCIB 11397 was grown and harvested by the method of Example 1. The yield of washed felt was 54 g wet weight, 7.5 g dry weight.

A portion of this felt (36 g wet weight, 5 g dry weight) was treated by the method of Example 3 to yield 2.17 g of solid product.

Analysis of the product indicated that it contained the same amino acids and sugars as that of Example 3. The immunostimulatory activity was also similar.

We claim:

1. A process for the production of a water-soluble fraction containing peptidoglycan material having immunostimulatory activity wherein the mycelium of a strain of Streptomyces griseus is treated with a bacteriolytic enzyme in an aqueous medium to solubilise bound peptidoglycan components of the cell walls thereof in said aqueous medium to yield a fraction containing the desired immunostimulatory activity, said process including the step of separating nucleic acid material from said peptidoglycan fraction.

2. A process as claimed in claim 1 wherein the mycelial cells are ruptured and the protoplasm washed from the insoluble cell-wall material prior to solubilisation of the peptidoglycan components.

3. A process as claimed in claim 1 or claim 2 wherein delipidation of the cell-walls is effected prior to peptidoglycan solubilisation.

4. A process as claimed in claim 3 wherein delipidation is effected by extraction with hot organic solvents or boiling aqueous detergent.

5. A process as claimed in claim 1 wherein whole mycelial cells are treated with an aqueous long-chain anionic wetting agent prior to peptidoglycan solubilisation whereby the whole cells are ruptured, the cell wall material is delipidated and the cell contents including nucleic acid material are removed.

6. A process as claimed in claim 1 wherein the bacteriolytic enzyme has endoacetylmuramidase activity.

7. A process as claimed in claim 6 wherein the bacteriolytic enzyme is egg white lysozyme.

8. A process as claimed in claim 1 wherein the treatment with the baterilolytic enzyme is effected in the presence of a bacteriostat.

9. A process as claimed in claim 1 wherein the cell wall material prior to peptidoglycan solubilisation or the solubilised peptidoglycan material is treated with at least one enzyme to remove nucleic acid material.

10. A process as claimed in claim 9 wherein the solubilised peptidoglycan material is treated with a ribonuclease and/or a deoxyribonuclease.

11. A process as claimed in claim 9 wherein the treatment to remove nucleic acid material is effected on the cell wall material prior to peptidoglycan solubilisation.

12. A process as claimed in claim 1 wherein the cell wall material prior to peptidoglycan solubilisation or the solubilised peptidoglycan material is treated with one or more proteolytic and/or glycolytic enzymes whereby proteins and/or carbohydrates are removed.

13. A process as claimed in claim 12 wherein the cell wall material or solubilised peptidoglycan material is treated with trypsin, chymotrypsin, pronase and/or α-amylase.

14. A process as claimed in claim 12 wherein the treatment to remove proteins and/or carbohydrates is effected on the cell wall material prior to peptidoglycan solubilisation.

15. A process as claimed in claim 1 wherein the aqueous solubilised peptidoglycan material is treated with an insolubilised proteolytic enzyme to remove any residual enzymes.

16. A process as claimed in claim 1 wherein the solubilised peptidoglycan material is subjected to molecular fractionation.

17. A process as claimed in claim 1 wherein the aqueous solubilised peptidoglycan material is freeze-dried.

18. A process as claimed in claim 1 wherein the strain of Streptomyces griseus is streptomycin-producing.

19. Water-soluble fractions containing peptidoglycan material having immunostimulatory activity whenever prepared by a process as claimed in claim 1.

20. Formulations comprising a product as claimed in claim 19 in an injectable vehicle or in the form of a liposome.

21. A process as claimed in claim 20 wherein ruptured cell walls of said mycelium are treated with a long-chain anionic wetting agent.

22. A process as claimed in claim 20 wherein said mycelium is ruptured with a long-chain anionic wetting agent.

23. A process as claimed in claim 21 or 22 in which said wetting agent is sodium dodecyl sulphate.

24. A fraction containing peptidoglycan material having immunostimulatory activity whenever prepared by a process as claimed in claim 20.

25. A process for the preparation of a fraction containing peptidoglycan material having immunostimulatory activity wherein mycelium of a strain of Streptomyces griseus is ruptured and delipidated and cell contents including nucleic acid material are removed therefrom.

* * * * *

UNITED STATES PATENT OFFICE
CERTIFICATE OF CORRECTION

Patent No. 4,157,278        Dated June 5, 1979

Inventor(s) Gordon W. ROSS et al.

It is certified that error appears in the above-identified patent and that said Letters Patent are hereby corrected as shown below:

In Claim 21, column 8, line 51, delete "20" and insert --25--.

In Claim 22, column 8, line 54, delete "20" and insert --25--.

In Claim 24, column 8, line 61, delete "20" and insert --25--.

Signed and Sealed this

Tenth Day of June 1980

[SEAL]

Attest:

SIDNEY A. DIAMOND

Attesting Officer   Commissioner of Patents and Trademarks